United States Patent [19]

Nakano et al.

[11] Patent Number: 5,510,501

[45] Date of Patent: Apr. 23, 1996

[54] SAINTOPIN DERIVATIVES

[75] Inventors: Hirofumi Nakano; Noboru Fujii; Yoshinori Yamashita; Yutaka Saitoh; Tsutomu Agatsuma; Katsuhiko Ando; Yasushi Nishiie, all of Machida; Katsunori Kita; Naoki Morishima, both of Shizuoka; Katsushige Gomi, Susono, all of Japan

[73] Assignee: Kyowa Hakko Kogyo, Co. Ltd., Tokyo, Japan

[21] Appl. No.: 256,711

[22] PCT Filed: Nov. 17, 1993

[86] PCT No.: PCT/JP93/01680

§ 371 Date: Jul. 21, 1994

§ 102(e) Date: Jul. 21, 1994

[87] PCT Pub. No.: WO94/12458

PCT Pub. Date: Jun. 9, 1994

[30] Foreign Application Priority Data

Jan. 12, 1992 [JP] Japan ................................ 4-321694

[51] Int. Cl.⁶ .................................................. C07C 49/423
[52] U.S. Cl. ................................................... 552/201
[58] Field of Search ...................................... 552/201

[56] References Cited

PUBLICATIONS

Yamashita, et al, *J. Antibiotics*, 43(10) 1344–6 (1990).
Fujii, et al, *J. Antibiotics*, 47(8) 949–51 (1994).
Yamachita, et al. "Induction of Mammalian DNA Topoisomerase I and II Mediated DNA Cleavage by Saintopin . . . ", Biochemistry 30: 5839–5845, 1991.
Bérdy, J. "Anthiacyclins" CRC Handbook of Antibiotic Compounds, vol. III, pp. 61–63, 1981.

*Primary Examiner*—Kimberly J. Prior
*Attorney, Agent, or Firm*—White & Case

[57] ABSTRACT

The present invention relates to Saintopin derivatives represented by the following formula (I):

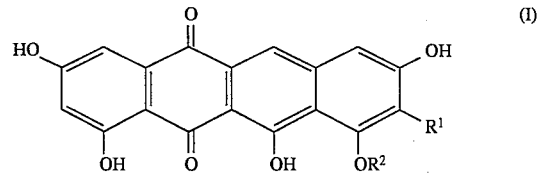

wherein $R^1$ is hydrogen and $R^2$ is $SO_2OH$ (UCE 1022), or $R^1$ is acetyl and $R^2$ is H (Saintopin E), which are useful as antibacterial and anti-tumor agents.

1 Claim, No Drawings

SAINTOPIN DERIVATIVES

This application is a 371 of PCT/JP93/01680.

TECHNICAL FIELD

The present invention relates to Saintopin derivatives which have antibacterial and anti-tumor activity and are useful as antibacterial and anti-tumor agents.

BACKGROUND ART

Heretofore, some compounds such as anthracycline have been reported as antibiotics having anthraquinone skeleton [CRC Handbook of Antibiotic Compounds, 3, 61 (1981)].

Further, UCT 1003 (Saintopin) having anti-tumor activity which is represented by the following formula A:

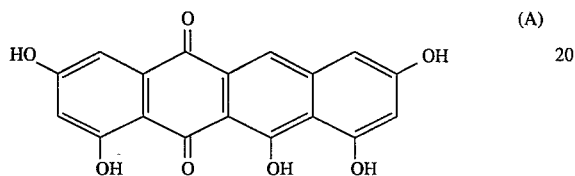

has also been known [Biochemistry, 30, 5838–5845 (1991); Japanese Published Unexamined Patent Application No. 200655/90].

DISCLOSURE OF THE INVENTION

The present invention relates to Saintopin derivatives having antibacterial and anti-tumor activity which are represented by the following formula (I):

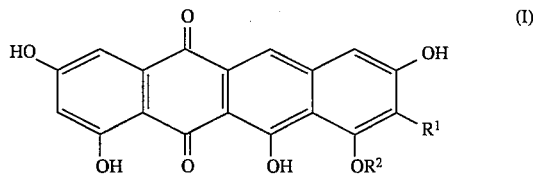

wherein $R^1$ is hydrogen and $R^2$ is $SO_2OH$ (hereinafter, the compound given by the definition is referred to as UCE 1022), or $R^1$ is acetyl and $R^2$ is hydrogen (hereinafter, the compound given by the definition is referred to as Saintopin E).

The compounds described above can be produced by culturing a microorganism belonging to the genus Paecilomyces.

The present invention is described in detail below.

The compound UCE 1022 has the following physicochemical properties.

(1) Molecular weight: 418
(2) Molecular formula: $C_{18}H_{10}O_{10}S$
(3) Mass spectrum:
  Secondary ion mass spectrum, negative mode (matrix: m-nitrobenzyl alcohol): m/z; 417(M—H)⁻
  High resolution FAB mass spectrum, negative mode (matrix: m-nitrobenzyl alcohol): m/z
  Found: 416.9919
  Calculated for $C_{18}H_9O_{10}S$: 416.9917
(4) UV absorption spectrum (measured in methanol) λmax nm (ε); 241 (22,000), 274 (27,500), 306 (16,100), 339 (9,800), 483 (12,300)
(5) IR absorption spectrum (measured by the KBr method): νmax cm⁻¹; 3360, 3210, 1625, 1600, 1400, 1330, 1265, 1235, 1045
(6) ¹³C-NMR spectrum (125 MHz, methanol-$d_4$ solution): δ ppm; 108.3, 109.2, 109.3, 111.4, 111.6, 114.8, 116.3, 121.9, 130.0, 137.5, 141.2, 154.3, 161.9, 166.4, 166.5, 166.6, 183.4, 190.8
(7) ¹H-NMR spectrum (500 MHz, methanol-$d_4$ solution): δ ppm; 6.57(1H, d), 7.09(1H, d), 7.21(1H, d), 7.41(1H, d), 7.96 (1H, s)
(8) Solubility:
  Soluble in water, methanol and ethanol, and sparingly soluble in n-hexane (UCT 1003 is sparingly soluble in water)
(9) Color reaction:
  Positive to the iodine and cerium sulfate-sulfuric acid tests
(10) Color and form of the substance:
  Reddish purple powder
(11) Thin layer chromatography:
  Rf value is 0.25 in silica gel thin layer chromatography (HPTLC plate Art. 5715, produced by Merck & Co., Inc.) with a developing solvent composed of n-hexane:ethyl acetate:methanol:acetic acid (6:4:1:1, v/v) (The spot of UCE 1022 is detectable by the absorption in the visible and UV regions).

Saintopin E has the following physicochemical properties.

(1) Molecular weight: 380
(2) Molecular formula: $C_{20}H_{12}O_8$
(3) Mass spectrum:
  High resolution FAB mass spectrum (matrix: m-nitrobenzyl alcohol): m/z
  Found: 381.3223 (M+H)⁺
  Calculated for $C_{20}H_{13}O_8$: 381.3214
(4) UV absorption spectrum (measured in methanol) λmax nm (ε); 290 (17,100), 338 (8,100), 566 (7,300)
(5) IR absorption spectrum (measured by the KBr method): νmax cm⁻¹; 3431, 3230, 1622, 1564, 1437, 1387, 1269, 1163
(6) ¹H-NMR spectrum (500 MHz, DMSO-$d_6$ solution): δ ppm; 14.10(1H, br.s), 13.43(1H, br.s), 10.76(1H, br.s), 7.46(1H, s), 7.04(1H, d, 2.1 Hz), 6.53(1H, d, 2.1 Hz), 6.34(1H, s), 2.66(3H, s)
(7) Solubility:
  Readily soluble in dimethyl sulfoxide (DMSO), methanol and acetone, soluble in chloroform and ethyl acetate, and sparingly soluble in water and n-hexane
(8) Color and form of the substance:
  Bluish purple powder
(9) Thin layer chromatography:
  Rf value is 0.50 in silica gel thin layer chromatography (HPTLC plate Art. 5715, produced by Merck & Co., Inc.) with a developing solvent composed of n-hexane:ethyl acetate:methanol:acetic acid (6:4:1:1, v/v)
(10) High performance liquid chromatography:
  Retention time; 8.56 min. (Column; YMC AM312 ODC, produced by YMC Corporation: Flow rate; 1 ml/min.:
  Mobile phase; a 70% methanol solution containing 5 mM ammonium acetate)

The biological activities of Compounds (I) are described below.

TEST EXAMPLE 1

Antibacterial activity

The minimum inhibitory concentration (MIC) against the growth of various bacteria is shown in Table 1. The antibacterial activity was determined by the agar dilution method using a medium (pH 7) which comprises 3 g/l Bacto-Tryptone (produced by Difco Laboratories), 3 g/l meat extract, 1 g/l yeast extract, 1 g/l glucose and 16 g/l agar.

TABLE 1

| Bacteria tested | MIC (µg/ml) (UCE 1022) |
| --- | --- |
| Staphylococcus aureus ATCC 6538P | 0.52 |
| Enterococcus faecium ATCC 10541 | 0.52 |

TEST EXAMPLE 2

Anti-tumor activity against HeLaS$_3$ cells

HeLaS$_3$ cells (ATCC HTB22) were suspended in a medium comprising 10% fetal calf serum, 2 mM glutamine and MEM medium (produced by Nippon Pharmaceutical Co., Ltd.) (hereinafter referred to as medium A) to a concentration of $3 \times 10^4$ cells/ml. The cell suspension was put into wells of a 96-well microtiter plate in an amount of 0.1 ml per well. The cells in the plate were cultured at 37° C. for 20 hours in a CO$_2$-incubator. Subsequently, the test compound appropriately diluted with medium A was added to the wells in an amount of 0.1 ml/well. The cells were further cultured at 37° C. for 72 hours in the CO$_2$-incubator, and then the culture supernatant was removed. To the residue was added a medium comprising medium A and 0.02% Neutral Red in an amount of 0.1 ml per well, followed by culturing at 37° C. for one hour in the CO$_2$-incubator, whereby the cells were stained. After removal of the culture supernatant, the residue was washed once with physiological saline. The pigment was extracted with 0.001N hydrochloric acid/30% ethanol, and the absorbance at 550 nm was measured by using a microplate reader. The concentration of the test compound at which the growth of the cells is inhibited by 50% (IC$_{50}$) was calculated by comparing the absorbance of untreated cells with those of the cells treated with the test compound at known concentrations. The result is shown in Table 2.

TABLE 2

| Test compound | IC$_{50}$ (µM) |
| --- | --- |
| UCE 1022 | 6.1 |

TEST EXAMPLE 3

Growth inhibition against BALB 3T3/H-ras cells

BALB 3T3/H-ras cells were suspended in F10 medium comprising 10% fetal calf serum, 100 units/ml penicillin and 100 mg/ml streptomycin (a product by GIBCO Company; hereinafter referred to as medium B) to a concentration of $2 \times 10^4$ cells/ml. The cell suspension was put into wells of a 96-well microtiter plate in an amount of 0.1 ml per well. The cells in the plate were cultured at 37° C. for 20 hours in a CO$_2$-incubator. Subsequently, the test compound appropriately diluted with medium B was added to the wells in an amount of 0.05 ml per well. The cells were further cultured at 37° C. for 72 hours in the CO$_2$-incubator. The system was treated in the same manner as in Test Example 2 to calculate the concentration of the test compound at which the growth of the cells is inhibited by 50% (IC$_{50}$). The result is shown in Table 3.

TABLE 3

| Test compound | IC$_{50}$ (µM) |
| --- | --- |
| Saintopin E | 2.4 |

The process for producing Compounds (I) is described below.

UCE 1022, which is included in Compounds (I), can be obtained by culturing a microorganism belonging to the genus Paecilomyces and having the ability to produce UCE 1022 in a medium, allowing UCE 1022 to accumulate in the culture, and recovering UCE 1022 from the culture.

As the UCE 1022-producing strains of the present invention, any strains which belong to the genus Paecilomyces and have the ability to produce UCE 1022 can be used. In addition, any mutants of such strains which are obtained by various artificial mutation methods such as UV irradiation, X ray irradiation and treatment with mutagens or by spontaneous mutation may also be used in the present invention, insofar as they have the ability to produce UCE 1022. A typical example of a suitable strain is UOE 1022 strain which has been isolated from soil by the present inventors.

The mycological properties of UOE 1022 strain are as follows.

1. Macroscopic observation

When UOE 1022 strain is cultured at 25° C. on a malt extract agar medium, the diameter of a colony reaches about 28 mm on the seventh day from the start of the culturing. The surface of the colony is floccose and shows a white color. The center of the back side of the colony shows an orange color, and the edge thereof shows a pale yellow color. In the culture medium, the dissolution of a soluble pale yellow pigment is observed.

When this strain is cultured at 25° C. on a potato glucose agar medium, the diameter of a colony reaches 26 to 27 mm on the seventh day from the start of the culturing. The surface of the colony is floccose, and the center thereof shows a lilac color or a purple color and the edge a white color to a gray color. The back side of the colony shows a lemon color. In the culture medium, the dissolution of a soluble pale yellow pigment is observed.

The optimum growth temperature for this strain is in the range of 11° to 34° C., and most preferably about 23° C. The pH range that allows its growth is 3 to 10.5, and the optimum growth pH is around 6.

2. Observation under optical microscope

UOE 1022 strain is cultured at 25° C. on a malt extract agar medium and is observed under the optical microscope. The results are as follows.

Hyphae are septate and smooth and branch well. Conidiophores arise from the hyphae, are colorless and smooth, and branch in the upper part in a verticillate form or irregularly. On the top of each branch of the conidiophores, two to four phialides are formed. In some cases, one to four phialides are formed directly on the top of each conidiophore. The phialides are colorless, smooth and lageniform, and taper off to a point. They are 7 to 12 µm long, and 2 to 3 µm wide at the part near its joint, tapering to about 0.5 µm wide. The conidial ontogeny is enteroblastic. Phialoconidia are unicellular and fusiform or limoniform in shape. They are colorless and smooth, and are 3 to 4.5 µm long and 1.5 to 2.5 µm wide. The conidia develop in the form of a long chain from the top of the phialide. Only the anamorph as described above is observed for this strain, with no teleomorph being observed at all.

A taxonomical study of this strain based on the above mycological properties according to "The Genera of Fungi Sporulating in Pure Culture, 2nd Ed., Cramer, Vaduz, J. A. von Arx, 1974" revealed that it belongs to the genus Paecilomyces, which falls under hyphomycetes.

The strain was named Paecilomyces sp. UOE 1022 by the present inventors and was deposited with the National Institute of Bioscience and Human Technology with accession number FERM BP-4066 on Nov. 5, 1992.

The process for producing Saintopin E is described below.

Saintopin E can be obtained by culturing a microorganism belonging to the genus Paecilomyces and having the ability to produce Saintopin E in a medium, allowing Saintopin E to accumulate in the culture, and recovering Saintopin E from the culture.

As the Saintopin E-producing strains of the present invention, any strains which belong to the genus Paecilomyces and have the ability to produce Saintopin E can be used. In addition, any mutants of such strains which are obtained by various artificial mutation methods such as UV irradiation, X ray irradiation and treatment with mutagens or by spontaneous mutation may also be used in the present invention, insofar as they have the ability to produce Saintopin E. A typical example of a suitable strain is SPC-13780 strain.

The strain has been deposited with the Fermentation Research Institute, Agency of Industrial Science and Technology under the Budapest Treaty with accession number FERM BP-2256 (date of original deposit: Jan. 24, 1989) (Japanese Published Unexamined Patent Application No. 00655/90).

The culturing methods for UCE 1022-producing strains and Saintopin E-producing strains are as follows.

For the culturing of the Saintopin derivatives-producing strains used in the present invention, conventional methods for culturing molds are generally employed. As the medium, either a synthetic medium or a natural medium may be used insofar as it appropriately contains carbon sources, nitrogen sources and inorganic substances which can be assimilated by the strains employed and the growth- and production-promoting substances required.

As the carbon sources, glucose, starch, dextrin, mannose, fructose, sucrose, lactose, xylose, arabinose, mannitol, molasses, etc. can be used alone or in combination. In addition, hydrocarbons, alcohols, organic acids, etc. may also be used according to the assimilability of the microorganism employed. As the nitrogen sources, ammonium chloride, ammonium nitrate, ammonium sulfate, sodium nitrate, urea, peptone, meat extract, yeast extract, dry yeast, corn steep liquor, soybean powder, casamino acid, etc. can be used alone or in combination. If necessary, inorganic salts such as sodium chloride, potassium chloride, magnesium sulfate, magnesium phosphate, calcium carbonate, potassium dihydrogenphosphate, ferrous sulfate, calcium chloride, manganese sulfate, zinc sulfate, copper sulfate, etc. may be added. In addition, trace ingredients that promote the growth of the strain employed and the production of the Saintopin derivatives may also be added to the medium.

As the method of culturing, liquid culture, especially submerged stirring culture, is preferably employed. Culturing is carried out at 16° to 37° C., preferably 25° to 32° C., and at pH 4 to 10, preferably 6 to 8. In general, by culturing for 1 to 7 days, the desired substance is produced and accumulated in the culture. In order to adjust the pH of the medium, aqueous ammonia, ammonium carbonate solution, etc. are used. When the amount of the product in the culture reaches the maximum, the culturing is discontinued.

For the isolation and purification of the desired substance from the culture, an ordinary method for isolating a microbial metabolite from the culture can be utilized. For example, the culture is separated into culture filtrate and microbial cells by filtration. The microbial cells are extracted with methanol, acetone, or the like. Then, the extract is mixed with the culture filtrate, and the resulting mixture is passed through a column of polystyrene adsorbent such as Diaion HP20 (produced by Mitsubishi Kasei Corporation) to adsorb the active component, followed by elution with ethyl acetate, acetone, or the like. The eluate is concentrated, and the concentrate is subjected to silica gel column chromatography, high performance liquid chromatography, and the like to obtain the desired substance. During the culture and purification steps, the desired substance can be traced by the UV absorbance of the substance.

Examples of the present invention are shown below.

BEST MODE FOR CARRYING OUT THE INVENTION

Example 1

Paecilomyces sp. UOE 1022 strain (FERM BP-4066) was used as the seed strain. The strain was inoculated into 300 ml of a seed medium having the following composition in a 2-1 Erlenmeyer flask, and cultured with shaking at 25° C. for 48 hours.

Composition of the seed medium (in 1 l): 5 g of peptone (Kyokuto Pharmaceutical Co. Ltd.), 5 g of dry yeast "Ebios", 10 g of glucose, 200 ml of V8 vegetable juice (Campbell Japan), 0.5 g of $Mg_3(PO_4)_2 \cdot 8H_2O$ (pH 6.0 before sterilization)

The resulting seed culture was transferred into 18 l of a fermentation medium having the following composition in a 30-l jar fermentor at the rate of 5% (by volume), and culturing was carried out at 25° C. with stirring and aeration (rotation: 300 rpm, aeration: 18 l/min.).

Composition of the fermentation medium (in 1 l): 50 g of soluble starch, 30 g of corn steep liquor (Japan Maize Products Co., Ltd.), 0.5 g of $KH_2PO_4$, 0.5 g of $MgSO_4 \cdot 7H_2O$, 0.5 g of $Mg_3(PO_4)_2 \cdot 8H_2O$ (pH 7.0 before sterilization, adjusted with NaOH)

Culturing was carried out for 144 hours without controlling the pH of the medium.

After the completion of culturing, 7.5 l of the fermentation culture was filtered and 10 l of methanol was added to the cell fraction, followed by stirring, whereby UCE 1022 was extracted. To the methanol extract was added 30 l of water, and the mixture was passed through a column packed with 0.5 l of a non-ionic porous resin, Diaion HP20 (produced by Mitsubishi Kasei Corporation), to adsorb the active substance. After impurities were eluted with methanol/water (30:70, v/v), the active substance was eluted with 1.5 l of methanol/water (50:50, v/v). The active fraction eluted was concentrated, and the concentrate was applied to a column packed with 0.5 l of silica gel (BW 300, produced by Fuji Devison Chemical Ltd.), followed by development with ethyl acetate/methanol/water (3:2:1, v/v). The active fraction thus eluted was concentrated, and the concentrate was applied to a column packed with 125 ml of silica gel (Lichroprep-Si 60, Art 9390; produced by Merck & Co., Inc.), followed by development with ethanol/water (100:3, v/v). The active fraction eluted was concentrated to dryness to give 20 mg of UCE 1022 as red powder.

Example 2

Paecilomyces sp. SPC-13780 strain (FERM BP-2256) was used as the seed strain. The strain was inoculated into 300 ml of a seed medium having the following composition in a 2-l Erlenmeyer flask, and cultured with shaking (200 rpm) at 30° C. for 48 hours.

Composition of the seed medium (in 1 l): 5 g of peptone, 5 g of dry yeast "Ebios", 10 g of glucose, 200 ml of V8 vegetable juice, 0.5 g of $Mg_3(PO_4)_2 \cdot 8H_2O$ (pH 6.0 before sterilization)

The resulting seed culture was transferred into 15 l of a fermentation medium having the following composition in a 30-l jar fermentor at the rate of 5% (by volume), and culturing was carried out at 30° C. with stirring and aeration (rotation: 400 rpm, aeration: 15 l/min.).

Composition of the fermentation medium (in 1 l): 35 g of glycerol, 35 g of glucose, 15 g of dry yeast, 0.5 g of $KH_2PO_4$, 0.5 g of $MgSO_4 \cdot 7H_2O$, 0.5 g of $Mg_3(PO_4)_2 \cdot 8H_2O$ (pH 7.0 before sterilization, adjusted with NaOH)

Culturing was carried out for 80 hours without controlling the pH of the medium.

After filtration of the resulting culture, 5 l of acetone was added to the obtained cells, followed by stirring. The removal of the cells and precipitates by filtration gave 5 l of a filtrate. To the filtrate were added 15 l of ethyl acetate and 0.5 l of ammonia. After stirring, the resulting mixture was passed through a column packed with 2 l of silica gel to adsorb the active substance. The active substance was eluted with acetone/ethyl acetate/ammonia (1:1:0.05, v/v). The active fraction was concentrated, and the concentrate was diluted with a 10 mM phosphate buffer (pH 8.0) and passed through a column packed with a polystyrene adsorption resin, Diaion HP20 (produced by Mitsubishi Kasei Corporation; 400 ml) to adsorb the active substance. After impurities were eluted with a 10 mM phosphate buffer (pH 8.0) and subsequently with 40% methanol containing the buffer of the same concentration, the active substance was eluted with 60% methanol. The active fraction was concentrated, and the concentrate was diluted with a 10 mM phosphate buffer (pH 8.0) and subjected to column chromatography using a polystyrene adsorption resin, Diaion HP20SS (produced by Mitsubishi Kasei Corporation; 200 ml). The 60% methanol-eluted solution was concentrated, and the concentrate was dissolved in a small quantity of a mixture of methanol and acetone. The active substance was precipitated from the solution by adding hexane. The precipitate was separated by filtration and dried to give 33 mg of Saintopin E as bluish purple powder.

Industrial Applicability

According to the present invention, Saintopin derivatives which have antibacterial and anti-tumor activity can be provided.

We claim:

1. Saintopin derivatives which are represented by the following formula (I):

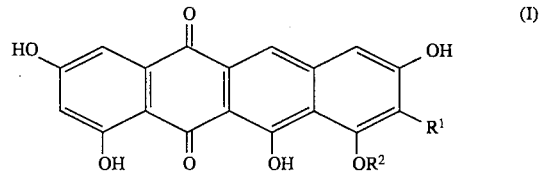

wherein $R^1$ is hydrogen and $R^2$ is $SO_2OH$, or $R^1$ is acetyl and $R^2$ is H.

* * * * *